(12) United States Patent
Marchand et al.

(10) Patent No.: US 11,635,362 B2
(45) Date of Patent: Apr. 25, 2023

(54) DEVICE AND METHOD FOR REAL-TIME DETECTION OF AEROPATHOGENS

(71) Applicant: AEROVIRUS TECHNOLOGIES INC., Saint-Hyacinthe (CA)

(72) Inventors: Norman Marchand, Saint-Hyacinthe (CA); Carmine Graziano, West Laval (CA)

(73) Assignee: AEROVIRUS TECHNOLOGIES INC., Saint-Hyacinthe (CA)

( * ) Notice: Subject to any disclaimer, the term of this patent is extended or adjusted under 35 U.S.C. 154(b) by 780 days.

(21) Appl. No.: 16/342,191

(22) PCT Filed: Nov. 15, 2016

(86) PCT No.: PCT/CA2016/051328
§ 371 (c)(1),
(2) Date: Apr. 15, 2019

(87) PCT Pub. No.: WO2018/090122
PCT Pub. Date: May 24, 2018

(65) Prior Publication Data
US 2019/0242807 A1    Aug. 8, 2019

(51) Int. Cl.
*G01N 15/06* (2006.01)
*G01N 15/02* (2006.01)
(Continued)

(52) U.S. Cl.
CPC ..... *G01N 15/0656* (2013.01); *B01D 11/0496* (2013.01); *B01L 3/50273* (2013.01);
(Continued)

(58) Field of Classification Search
CPC .... C12Q 1/70; C12Q 1/6804; G01N 33/5308; G01N 15/0266; G01N 15/0606;
(Continued)

(56) References Cited

U.S. PATENT DOCUMENTS

| 4,941,899 A | 7/1990 | Liu |
| 6,190,548 B1 * | 2/2001 | Frick ...................... C02F 3/288 210/252 |

(Continued)

FOREIGN PATENT DOCUMENTS

CA    2898714    1/2017

OTHER PUBLICATIONS

Supplementary Partial European Search Report, Application No. 16921915.1-1001 / 3512933, dated Apr. 17, 2020.
(Continued)

*Primary Examiner* — Dean Kwak
(74) *Attorney, Agent, or Firm* — Fresh IP, PLC; Clifford D. Hyra; Aubrey Y. Chen

(57) ABSTRACT

The invention provides a device and method for the real-time detection of aeropathogens. The device includes an aerosampler having an air inlet and at least one collector tube, a microfluidic system which includes a container, piping, a micro pump for flowing a liquid and a viral detection chamber. The viral detection chamber has an electrode which may be equipped with functionalized bio sensors, a counter electrode, an electronic detection system connectable to the electrodes of the viral detection chamber, and an embedded electronic processing system for processing data from the electronic detection system.

8 Claims, 9 Drawing Sheets

(51) Int. Cl.
*B01D 11/04* (2006.01)
*G01N 27/00* (2006.01)
*B01L 9/00* (2006.01)
*B01L 3/00* (2006.01)
*B01L 5/00* (2006.01)
*G01N 33/569* (2006.01)
*C12Q 1/70* (2006.01)
*G01N 15/00* (2006.01)
*G01N 27/447* (2006.01)
*G01N 15/04* (2006.01)
*C12Q 1/6804* (2018.01)

(52) U.S. Cl.
CPC ........... *B01L 3/502715* (2013.01); *B01L 5/00* (2013.01); *B01L 9/527* (2013.01); *G01N 15/0255* (2013.01); *G01N 15/0266* (2013.01); *G01N 15/042* (2013.01); *G01N 15/0606* (2013.01); *G01N 27/00* (2013.01); *G01N 33/56983* (2013.01); *B01L 2300/0636* (2013.01); *C12Q 1/6804* (2013.01); *C12Q 1/70* (2013.01); *G01N 27/44791* (2013.01); *G01N 2015/0065* (2013.01); *G01N 2015/0288* (2013.01)

(58) Field of Classification Search
CPC ....... G01N 15/0656; G01N 2001/2223; G01N 2001/4083; G01N 2015/0065; G01N 2015/0288; G01N 33/56983; G01N 2015/0038; G01N 33/569; G01N 15/042; G01N 27/00; G01N 27/44791; B01L 2300/0636; B01L 3/502715; B01L 3/50273; B01L 5/00; B01L 2300/0645; B01L 2400/049; B01L 9/527; B01D 11/0496

See application file for complete search history.

(56) References Cited

U.S. PATENT DOCUMENTS

| 8,686,709 | B2 | 4/2014 | Tartagni | |
| 2007/0186696 | A1 | 8/2007 | Pletcher | |
| 2019/0154550 | A1* | 5/2019 | Wu | G01N 1/2214 |
| 2019/0232282 | A1* | 8/2019 | Pierson | C12Q 1/6804 |

OTHER PUBLICATIONS

Luke Brockman: "University of Arkansas, Fayetteville QCM Aptasensor for Rapid and Specific Detection of Avian Influenza Virus Recommended Citation Brockman, Luke, "QCM Aptasensor for Rapid and Specific Detection of Avian Influenza Virus, Jan. 1, 2013 (Jan. 1, 2013), XP055680024, Retrieved from the Internet: https://scholarworks.uark.edu/ogi/viewcontent.cig?article=1788&context=etd.

International Search Report, International application No. PCT/CA2016/051328, dated Aug. 2, 2017.

* cited by examiner

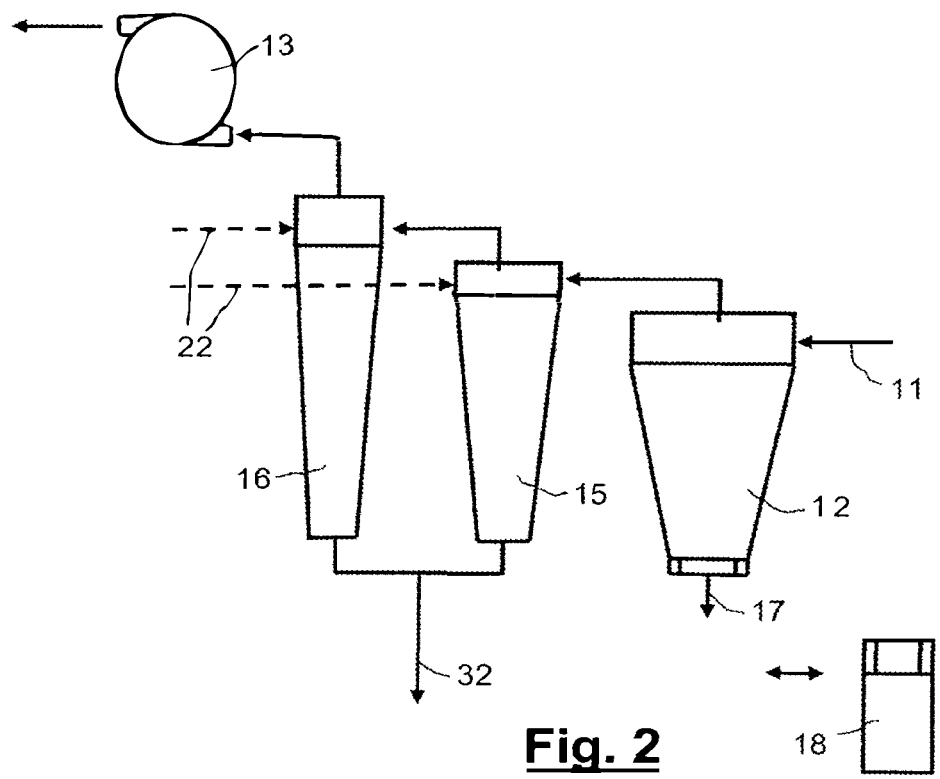
Fig. 2
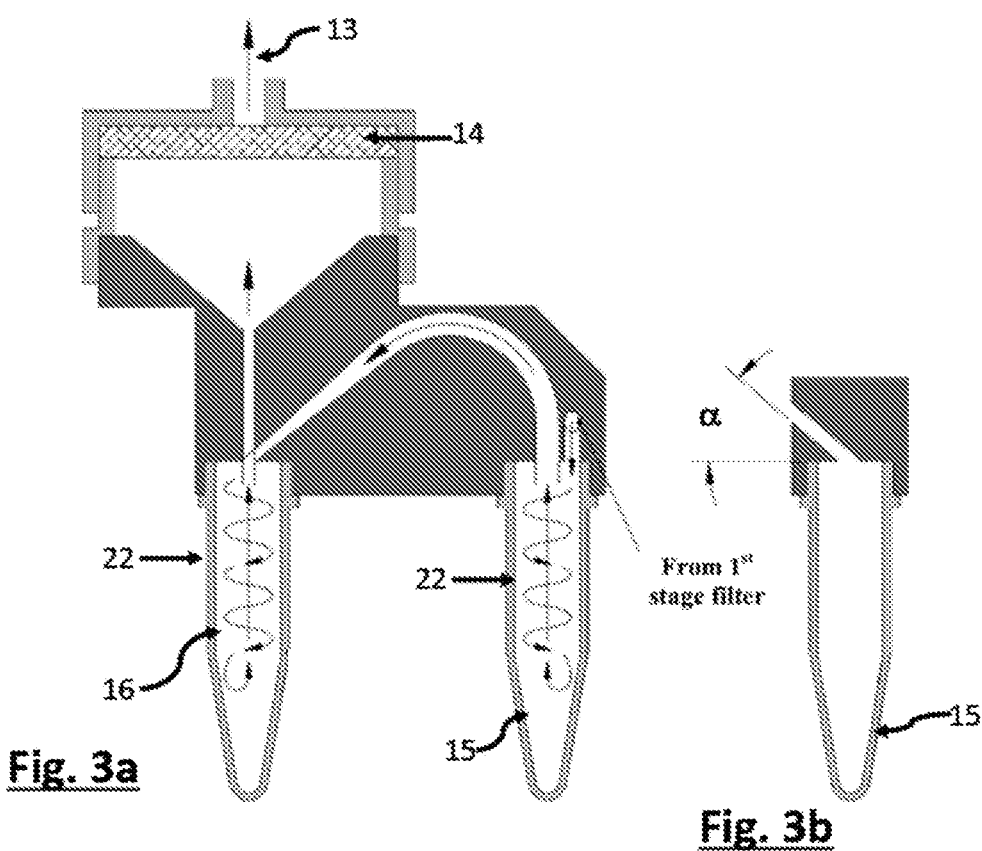
Fig. 3a
Fig. 3b

```
Moistening Container 2
        ↓
Pressure Pump 21
        ↓
Flow rate controller # 1
        ↓
Collector tubes 15, 16
        ↓
Viral detection chamber 4
        ↓
Flow rate controller # 2
        ↓
Suction pump 91
        ↓
Waiste container 9
```

Fig. 6

DEVICE AND METHOD FOR REAL-TIME DETECTION OF AEROPATHOGENS

FIELD OF THE INVENTION

The present invention relates to the detection of pathogens, including aeroviruses and aerobacteria, such as SIV (swine Influenza virus) and/or PRRSV (porcine respiratory and reproductive syndrome virus), and/or MH (*Mycoplasma* Hyopneumoniae) in any environments where swine herds might be exposed to, or other aeropathogens that affect human populations and/or various animal farm industries including poultry.

BACKGROUND

Simply defined, tiny droplets suspended in air and containing biological materials like viruses, bacteria, and fungi are called "bioaerosols". For most animal species, the organ that is most sensitive to bioaerosol exposure is the respiratory tract system. Our respiratory system is efficient in removing aerosols, but if the particle size falls below a particular range or the particles highly concentrated, they can cause health effects. In fact, very small particles (≤5 μm) can reach the pulmonary alveolar and cause severe respiratory illnesses in humans and animals.

Furthermore, it has been recently demonstrated that transmission of SIV, PRRSV, and MH via bio-aerosol is more efficient than spread through contaminated environmental surfaces/fomites, and that transmission via aerosols now accounts for more than 53% of all infections. Given the right atmospheric conditions, aeropathogens such as the SIV, PRRSV, and MH bio-aerosols, have been shown to travel up to 9.2 km and 4.7 Km respectively, proving that long distance airborne transport of aeropathogens occurs.

Currently, all existing detection systems for aeropathogens require more than 16 hours for collecting and analyzing samples, and therefore are not suited for screening potential pathogen carriers. Furthermore, there is no commercially available instrument capable of measuring in real time the type and concentration of airborne viruses or airborne bacteria.

OBJECTS

An object is to provide a device and a method for real-time detection of aeropathogens.

Real-time within the meaning of the present disclosure means that a detection result shall be available within half an hour, preferably within 15 minutes, most preferred within 5 minutes, from starting the detection procedure, namely the first air introduced into the aerosampler as explained below.

Another object is to provide a device and a method to identify specific aeropathogens.

Another object is to provide a device and a method to identify quantitatively the concentration of specific aeropathogens present in the air.

Still another object is to detect different aeropathogens simultaneously.

Still another object is to provide a device for detecting aeropathogens which device can be used multiple times by an automatic cleansing and refreshing system.

Still another object is to provide a device and method for detecting aeropathogens, which is easy to handle by medical laymen, such as farmers and custom executives.

SUMMARY

We disclose a device for real-time detection of aeropathogens comprising an aerosampler having an air inlet, a microfluidic system comprising at least one container, piping and at least one micro pump for flowing a liquid, at least one viral detection chamber, each of the at least one viral detection chambers having at least a working electrode apt to be equipped with functionalized biosensors and at least one counter electrode, at least one electronic detection system connectable to the electrodes of the at least one viral detection chamber, and an electronic processing system processing data receivable from the at least one electronic detection system.

In an embodiment, the aerosampler comprises an optional dust collector, a first aeropathogen collector tube, a second collector tube and an air pump conveying ambient air first through the dust collector, if any, then through the first and second collector tubes. The first collector tube is adapted to collect larger aerosol particles, preferably having a diameter from about 2 μm to about 10 μm, and the second collector tube is adapted to collect smaller aerosol particles, preferably having a diameter of up to 5 μm. The inlet to the collector tubes is eccentric to the tube axis and oblique versus the bottom of the tubes such that injected air moves centrifugally along the walls of the collector tubes and thereby throw entrained aerosol particles against the wall of the tubes. Such small particle collectors are known in the art as "reverse flow cyclones", e.g. from U.S. Pat. Nos. 4,941,899 and 8,205,511. The dust collector preferably also works with centrifugal forces.

During collecting aerosol particles the walls of the collector tubes are preferably continuously wetted from the at least one liquid container. The wetting liquid (a suitable buffer liquid) collected in the collector tube is continuously or batchwise conveyed to the viral detection chamber.

The electrodes of the viral detection chamber are of noble metal such as Ag, Au, Pt, Ru or their alloys, preferably Au. The surface of the electrodes is preferably covered with a suitable binding agent for the aeropathogen to be detected, preferably with a self-assembled monolayer of aptamers specific to the aeropathogen to be detected.

The electrodes of the viral detection chamber are biased with a suitable voltage, preferably of between −300 mV and +50 mV and the response of the system in the range of 20 pA and 20 μA is measured by a lock-in phase amplification circuitry operating at low frequency, preferably below 400 Hz. Alternatively, ultra low noise DC current amplifiers can be used although more expensive than lock-in amplifiers operating in the same current range.

Preferably, several viral detection chambers are present in parallel, detecting either the same aeropathogen and averaging the result, or detecting different pathogens. Each viral detection chamber has an independent lock-in phase amplification circuitry. Preferably, the several lock-in phase amplification circuitries use one common oscillator. The measured data are stored and processed in a computer, e.g. compared with previously stored calibration data to identify presence and concentration of aeropathogens in the air introduced in the aerosampler.

Preferably, the device comprises a number of containers for storing and providing different liquids, such as the wetting liquid for the collector tubes, various cleaning liquids including deionized water, acids such as concentrated $H_2SO_4$, for cleaning the viral detection chamber, the pipes and the collector tubes, etc., and liquids for refreshing the electrode surfaces. The liquid from the containers may be conveyed by a common micropump and a common tube connected by a three-way valve to the tube connecting the collector tubes with the viral detection chamber, if the containers are provided with shut-valves, each.

Preferably the device comprises an additional container at the outlet side of the viral detection chamber, for collecting waste, namely used liquids. Waste liquids are conveyed to the waste container by an additional micropump.

Preferably, the pumps, valves, flow rates and the electronic detection systems are controlled by an embedded electronic system (electronic processing system), programmed to make the different elements act according to a preselected scheme.

The invention also comprises a method for real-time detection of aeropathogens by providing an aerosampler having an air inlet and comprising at least one collector tube, a microfluidic system comprising at least one container, piping and at least one pump for flowing a liquid, at least one viral detection chamber having at least two electrodes and being equipped with functionalized biosensors, at least one electronic detection system connectable to the electrodes of the at least one viral detection chamber, and an electronic processing system processing data receivable from the at least one electronic detection system, the method comprising moistening the walls of the at least one collector tube, introducing air into the aerosampler, collecting aeropathogens at the moist walls of the aerosampler, flowing moisture from the walls of the aerosampler to the viral detection chamber, detecting electric response between the electrodes of the viral detection chamber, and processing the electric response in the electronic processing system to identify the presence of aeropathogens in the air.

Aptamers

Aptamers are specific oligonucleotides composed of single stranded DNA (ssDNA) or RNA that bind to a wide range of targets specifically. Aptamers can be obtained using an in vitro selection procedure called Systematic Evolution of Ligands by EXponential enrichment (SELEX), that starts with the incubation of random oligonucleotide libraries with the desired target molecules, followed by the separation and amplification of bound oligonucleotides. By repeating this process, an enriched pool is obtained, which can be used as a starting library for the next round of selection to attain high specificity and affinity to the target molecules. In principle, aptamers can be selected for any given target, ranging from small molecules to large proteins and even cells. When aptamers bind small molecular targets, these get incorporated into the nucleic acid structure, buried within the binding pockets of aptamer structures. On the other hand, large molecules (e.g. proteins) are structurally more complicated, allowing aptamer interactions at various sites via hydrogen bonding, electrostatic interactions and shape complementarity. The production of aptamers is not costly, and they are very low in batch-to-batch variation compared to the antibodies produced in vivo. In addition, aptamers can be chemically synthesized, are thermally stable, and are suitable for long-term storage. With these advantages, aptamers with high specificity and affinity have been developed for a variety of targets, including proteins, small molecules, whole cells, and viruses. Aptamers are now been widely used in diverse fields, such as diagnostics, therapeutics, and biosensors. While aptasensors emerged only about 10 years ago, they have already found broad applications in both basic research and biomedical diagnostics.

Aptamer-based biosensors possess unprecedented advantages compared to biosensors using natural receptors such as antibodies and enzymes:

First, aptamers with high specificity and affinity can be selected in vitro for any given target, ranging from small molecules to large proteins and even cells, thus making it possible to develop a wide range of aptamer based biosensors.

Second, aptamers, once selected, can be synthesized with high reproducibility and purity from commercial sources. Also, in contrast to protein-based antibodies or enzymes, DNA aptamers are usually highly chemically stable.

Third, aptamers often undergo significant conformational changes upon target binding. This offers great flexibility in design of novel biosensors with high detection sensitivity and selectivity.

Fourth, the small size of aptamers provides advantages over antibodies: (i) a greater surface density of receptors and (ii) multiple binding to target molecules for sandwich assays.

Aptamers can be attached to the solid support at either the 5'-end or the 3' end. Particularly, gold is broadly used as the target. Direct attachment of aptamers to gold surfaces could be achieved by using a thiol-alkane linked to the aptamer sequence. The gold surface could also be functionalized and the type of chemistry selected is dependent on what type of terminal functional group is linked to the aptamer (i.e. amine, thiol or biotin termini).

Gold surfaces functionalized with self-assembled monolayers (SAMs) can address the nonspecific adsorption of aptamer to the surface. Avidin-biotin technology has also been exploited for aptamer immobilization. Strepavidin can be physically adsorbed or covalently immobilized onto the support and the method mainly requires incubation of the biotin-tethered aptamer with the modified substrate. Studies of the anti-thrombin aptamer revealed that this biocoating method gives best results regarding sensitivity compared to other immobilization strategies.

The invention preferably makes use of aptamers for binding the pathogens on the electrodes of the viral detection chamber.

BRIEF DESCRIPTION OF THE DRAWINGS

FIG. 2 shows a preferred design of the aerosampler;

FIGS. 3a and 3b show the preferred collector tubes in detail;

FIG. 6 shows the flow of the wetting fluid during continuous flow measurement;

Equal numerals in different drawings designate the same functional elements.

DETAILED DESCRIPTION

Figure 1:
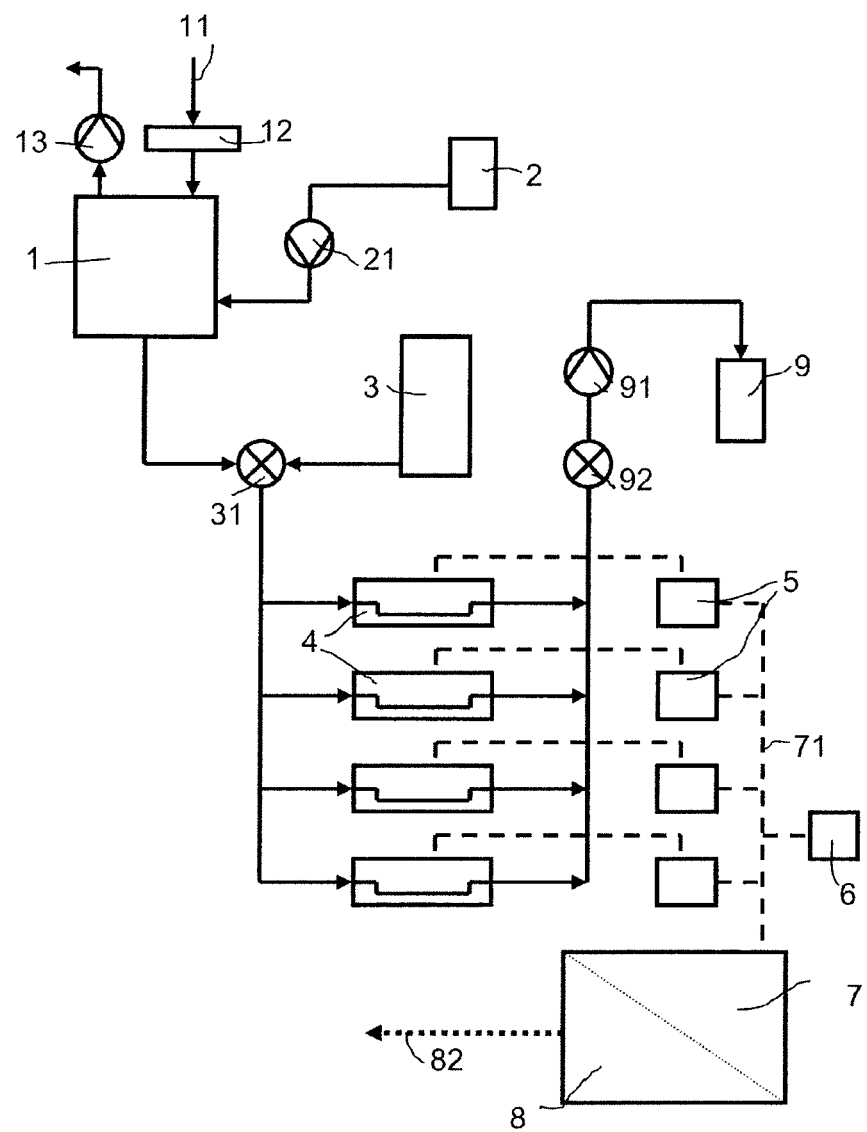
FIG. 1 shows an overall diagram of a preferred design of the device.

With reference to FIG. 1, numeral 1 designates the aerosampler. A gas pump 13 sucks in air from the air inlet 11, preferably equipped with a dust collector 12. Within the aerosampler 1 small particle droplets entrained in the air are separated and collected as explained in in more detail with reference to FIGS. 2 and 3 below. Wetting liquid (buffer solution) is conveyed from container 2 by means of a micropump 21 into the aerosampler. The buffer solution with collected droplets is conveyed to the at least one viral detection chamber 4; shown are four viral detection chambers 4 in parallel, allowing for detecting four different aeropathogens simultaneously. To each of the viral detection chambers 4 is assigned an electronic detection system 5 with a common oscillator 6. The dashed lines represent electric connecting lines. Measured signals from the viral detection chamber 4 are electronically stored and processed in a computer 7. An assembly of liquid containers 3 containing liquids for cleaning, rinsing and refreshing may be included in the liquid circuit by three-way valve 31. These liquids may be conveyed by a micropump 91 (suction side of the pump) to the viral detection chamber 4 and after use to a waste container 9. Pump 91 also helps conveying the buffer solution from the aerosampler 1 to the viral detection chamber 4. Valve 92 is open when the detection scan is made with continuously flowing buffer solution through the viral detection chamber 4 and is closed when the detection scan is made batchwise, namely non-flowing buffer solution. All functions of the pumps, valves and electronic detection systems 5 are controlled via control lines 82 to controller (the embedded electronic system) 8 according to a preselected procedure. Preferably pump 92 provides a variable flow rate of from 15 nanoliters (nL) per minute to 15 µl per minute. Two pumps may be installed in parallel, one allowing high flow rates and the other low flow rates, which may be run alternatively.

With reference to FIG. 2, in a preferred embodiment air is conveyed by suction of pump 13 from air inlet 11 through micro-centrifuges 12, 15 and 16. Numeral 12 designates a durst filter. Preferably pump 13 is set at a flow rate of between 3.5 to 7.5 liters per minute (normal pressure). The dust outlet 17 may be equipped with a dust container 18 for collecting dust particles of diameter of above about 10 µm. The walls of the collector tubes 15 and 16 are wetted via line 22 from the wetting liquid container 2 (FIG. 1). Collector tube 15 preferably mainly collects particles with a diameter of from 2 µm to 10 µM, whereas collector tube 15 is adapted to collect particles mainly with diameter up to 5 µm. The wetting liquid having caught particles from the air collect on the bottom of the collector tubes 15 and 16 is conveyed via line 32 to the viral detection chamber 4. The collector tubes preferable have a total inner volume of between 1 ml and 2.5 ml.

FIG. 3a shows the airflow through the collector tubes 15 and 16. FIG. 3b shows collector tube 15 turned by 90° around its axis as compared to FIG. 3a. Air is injected in each case eccentrically and oblique to the bottom of the tube to create centrifugal force for separation of the particles entrained in the air.

Figure 4:
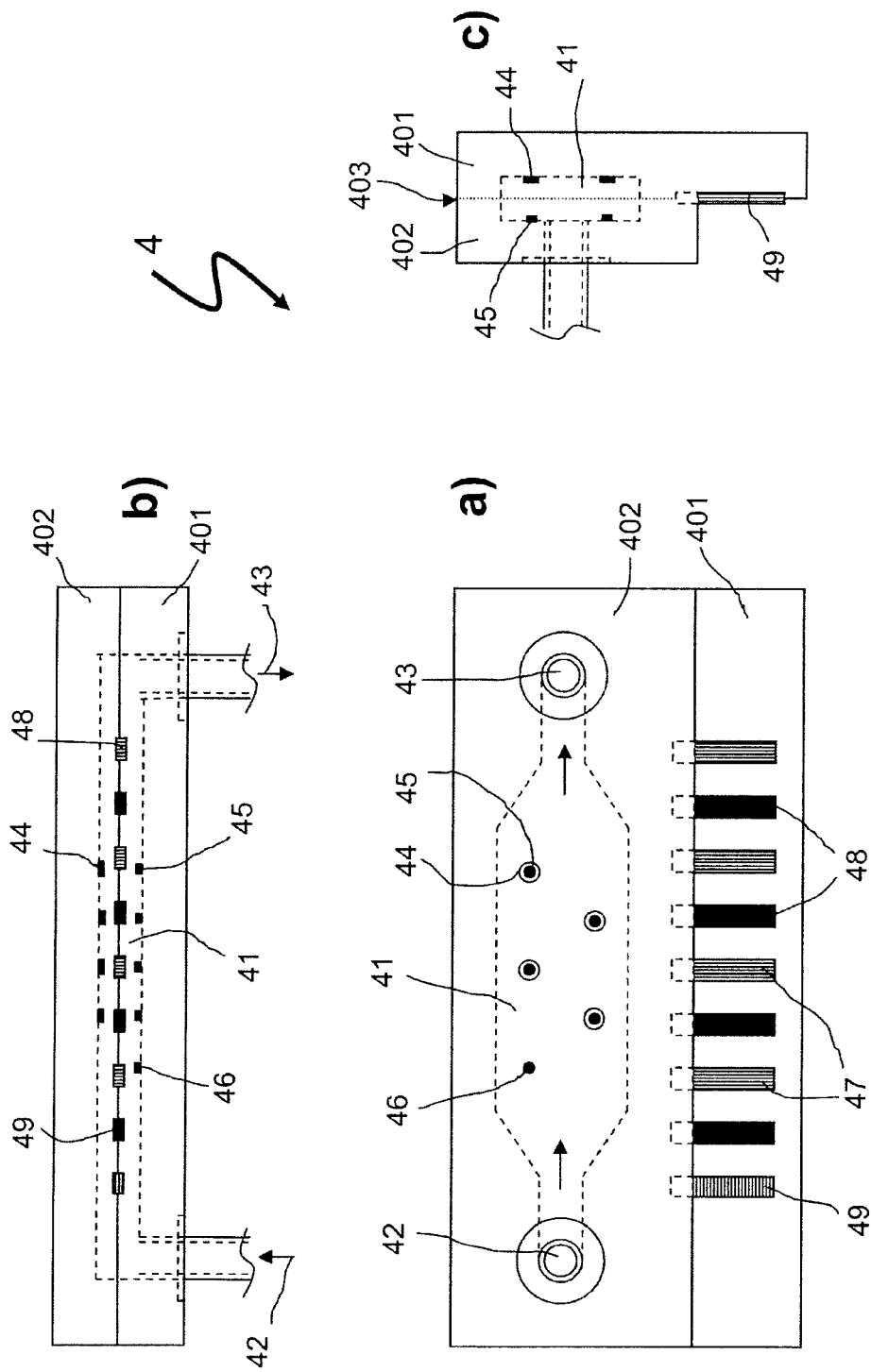
FIG. 4 shows the viral detection chamber.

FIG. 4 shows the viral detection chamber in detail. FIG. 4a) shows a top view, FIG. 4b) shows a side view and FIG. 4c) shows a front view. The designation of top, side or front view is only for defining the relative position of FIGS. 4 a), 4b) and 4c. The viral detection chamber may be arranged in any position, e.g. the front view may be the upper wall. The viral detection chamber, generally designated with 4, comprises an inner cavity 41 within a housing 401, 402 with an inlet 42 and an outlet 43. The arrows indicate the flow direction of the fluid received from the aerosampler 1. Preferably, the cavity 41 has a volume of between 0.5 and 1.5 mm$^3$. A volume of between 0.6 to 1 mm$^3$ is particularly preferred. The cavity 41 has parallel upper and lower walls carrying a number of counter electrodes 44 and working electrodes 45 opposite to each other. Preferably counter electrodes 44 are larger than the working electrodes that are carrying the binding agent for the aeropathogens. The smaller electrodes are the working electrodes. The distance between the working electrodes and the opposite counter electrode preferably is between 30 µm and 50 µm. The diameter of the counter electrodes 44 is preferably between 50 µm and up to 100 µm. The diameter of the working electrodes is preferably between 0.4 to 0.7 times the diameter of the counter electrodes. Each pair of working electrode and the opposite counter electrode create an electric field which is perpendicular to the flow direction of liquid. The distance of neighbouring counter electrodes is 15 to 30 times larger than their diameter. The electrodes are connected to connector terminals 47 and 48 as will be explained with reference to FIG. 5. An additional electrode 46 with connector terminals 49 serves as reference electrode. There is no working electrode opposite to the reference electrode. During detection the working electrodes are at a variable biasing voltage of −370 and +50 mV against the counter electrodes.

The housing of the viral detection is composed of two plates of preferably borosilicate float glass 401 and 402. Two holes 42 and 43 are drilled through one of the plates 402. Then the cavity is prepared by a reactive ion-$CF_4$ plasma etch technique. It may be sufficient to provide a cavity in only one of the plates.

Figure 5:
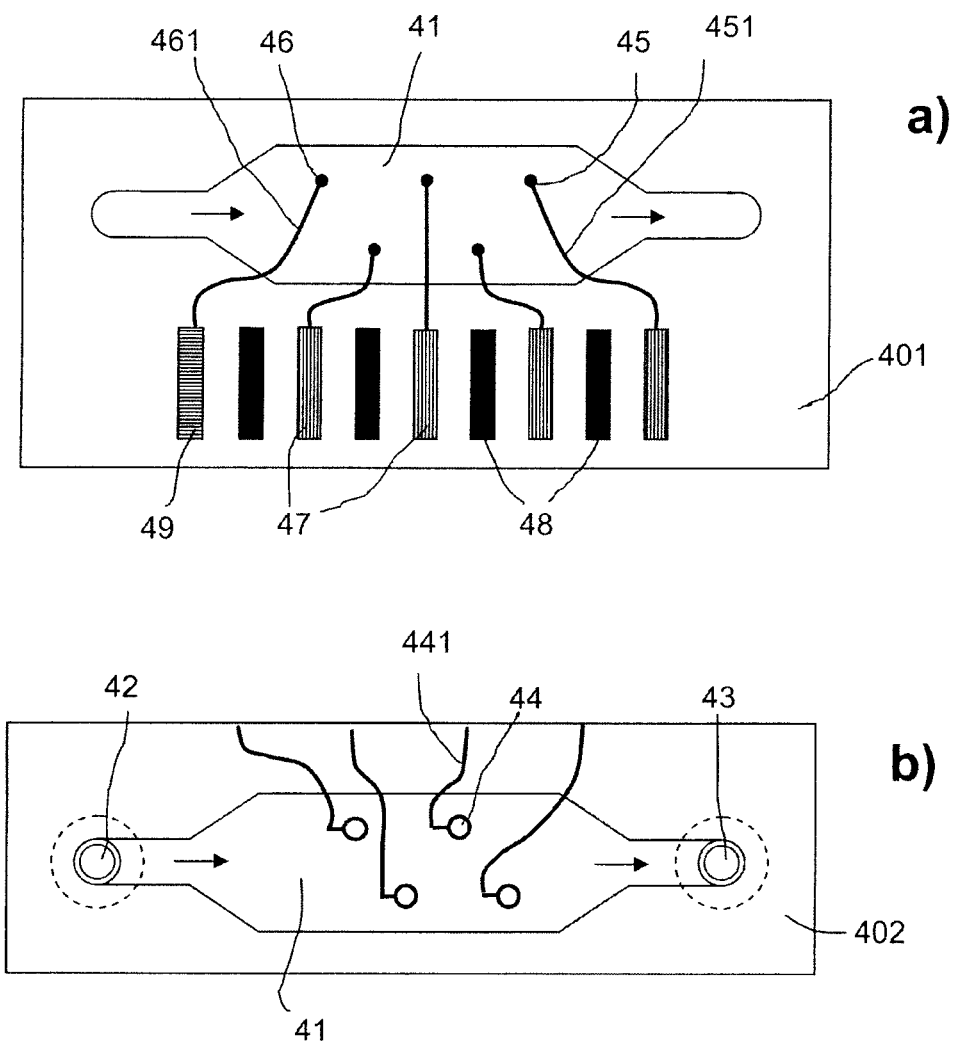
FIG. 5 illustrates the construction of the viral detection chamber.

FIGS. 5 a) and b) show the two plates 401 and 402 with their partial cavities on top. After providing the cavity 41, electrodes 44, 45 and 46, the connector terminals 47, 48 and 49 and the lines 441, 451 and 461 are applied to the plates by known photolithographic technique and deposition of noble metal vapour. The connecting lines 441, 451 and 461 are isolated by a suitable cover layer, e.g. of $SiO_2$. After removal of any organic material from the surface of the plates, the plates are aligned to each other as indicated by the dotted line 403 in FIG. 4c). The exactly aligned plates 401 and 402 are then fused by heating to between about 500° C. and 650° C. under high pressure perpendicular to the fuse line 403.

FIG. 6 is a flow chart showing the flow of the wetting fluid from the moistening container to the waste container with flow rate controllers #1 and #2 cooperating with the controller 8.

Figure 7:
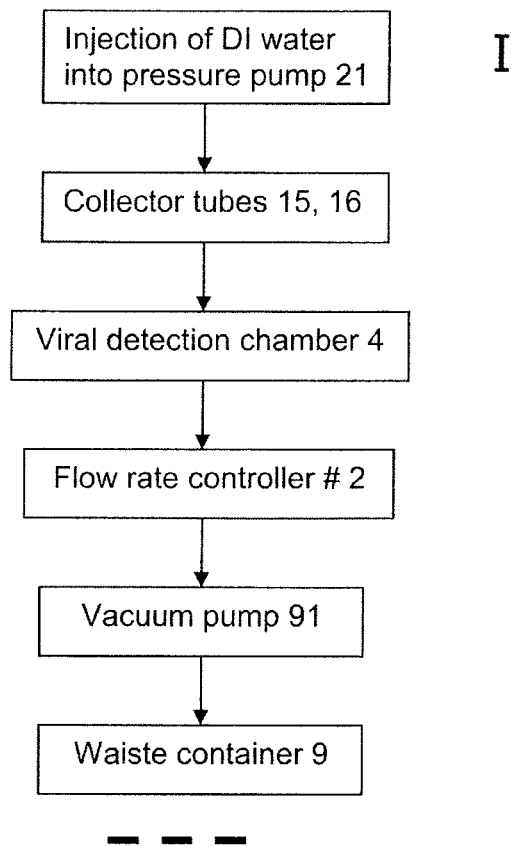
FIG. 7 shows the cleaning procedure.
Figure 7:
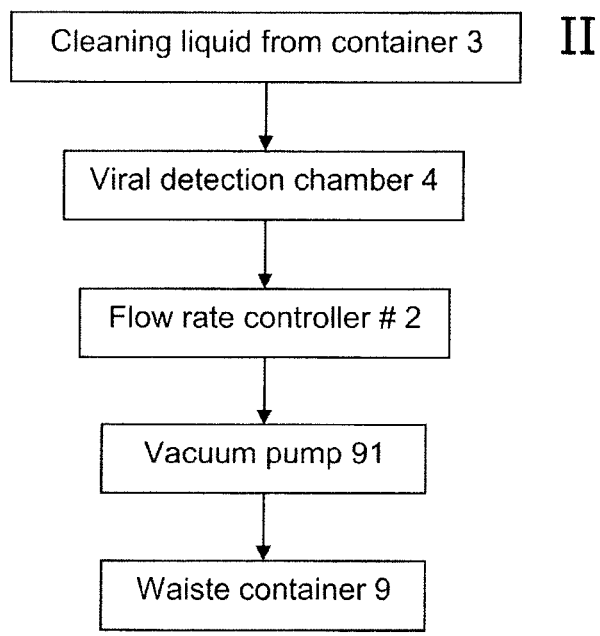

FIG. 7 is a flow chart showing the cleaning/refreshing procedure. First (I) deionized water is conveyed through the device. Thereafter (II) cleaning liquid e.g. concentrated $H_2SO_4$ is flown through the viral detection chamber 4 from one of the containers 3, followed by rinsing with deionized water from another container 3. This may be repeated several times until constant current is measured from the electrodes of the viral detection chamber 4. Thereafter refreshing liquid is conveyed from another container 3. Refreshing liquid contains the functionalized aptamers (for a given aeropathogen) that will form the self-assembled monolayer on the working electrode.

Figure 8:
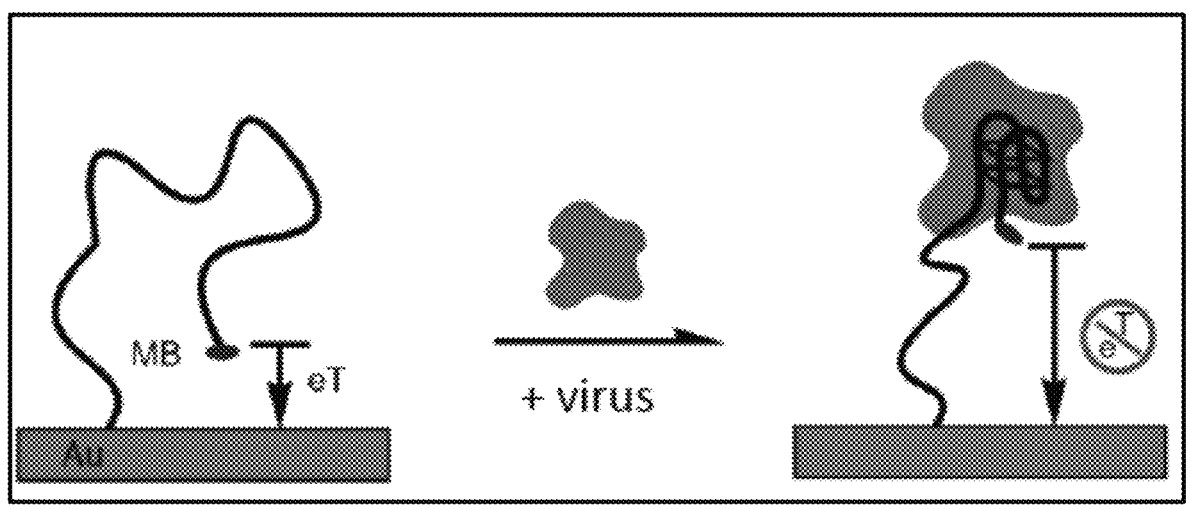
FIG. 8 shows schematically the binding mechanism of a virus to a gold electrode.

FIG. 8 shows a typical binding mechanism for aeropathogens. First, the self-assembled monolayer on the working electrode is produced according known technique. In our initial experiments we used an amino- and thiol-modified aptamer having a methylene-blue reporter group in a 0.5 to about 1 µmolar aqueous buffer solution through the viral detection chamber. The formula of the self-assembled monolayer of aptamers was

5'-HS—$(CH_2)_6$-GCAGT APTAMER ACTGCT-$(CH_2)_7$—$NH_2$-MB-3'.

or

5'-MB-NH$_2$—(CH$_2$)$_7$-TCGTCA-
APTAMER-TGACG-(CH$_2$)$_6$—HS-3'.

The left picture in FIG. 8 shows a single aptamer bound to a gold surface. The viral detection chamber is then rinsed with deionized water to remove the buffer solution.

Thereafter the liquid from the collector tubes is fed to the viral detection chamber. If aeropathogens are present in the liquid, what is indicated by the arrow and "virus" in the middle of FIG. 8, the aeropathogens binds to the aptamer by emitting an electron causing a response to the electronic detection system. After completion of the measurement, the viral detection chamber is rinsed with deionized water to remove all aeropathogens.

Figure 9:
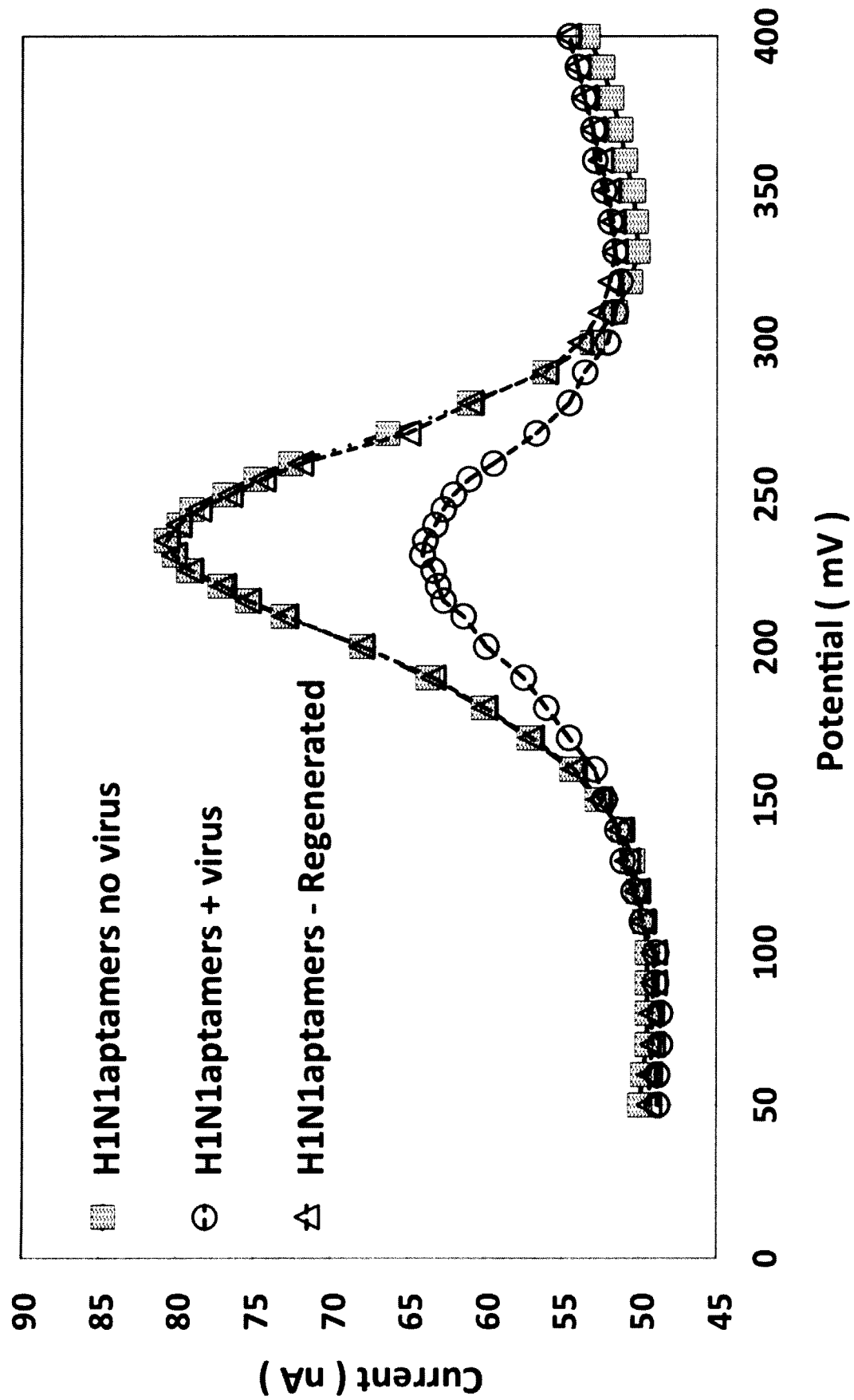
FIG. 9 shows a graph of a typical detection cycle as obtained by the present invention.

FIG. 9 shows a typical detection cycle, wherein the x-axis represents the bias-voltage and the y-axis represents the measured current. The upper solid curve obtained with no virus in the air is the calibration curve taken before each detection of ambient air.

The lower dashed curve is obtained with viruses in the air. From the difference of areas below both curves, it is possible to estimate the concentration of virus in the air. Even if the aptamer is unspecific to the aeropathogen, information on the type of aeropathogen may be obtained from position of the maximum of the upper curve on the x-axis may. The upper dashed curve is obtained after removal of the aeropathogens of a previous detection for calibration for the next detection cycle.

Figure 10:
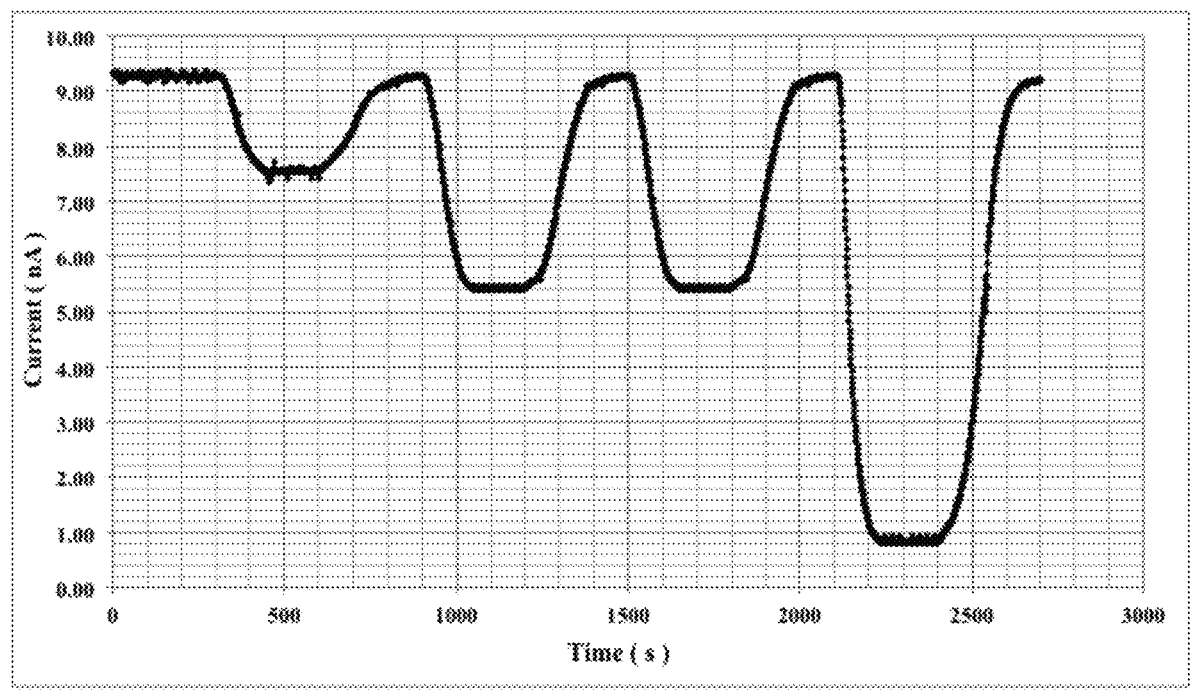
FIG. 10 shows examples of response of the system to different concentrations of a virus.

FIG. 10 demonstrates preliminary experiments showing the electronic response of the system as a function of virus concentration. The detection chamber is first floated with a solution containing S1+H1N1-aptamers to cover the working electrodes with such aptamers. Then, deionized water is fed from one of the containers 3 to remove any buffer solution for 5 min (time 0-300 s of the diagram). Thereafter the biasing voltage is set to 235 mV for optimal binding and virus carrying air at a concentration of 200 nMol/l (represented as the concentration of Hemaggluttinin as measured by PCR=polymerase chain reaction)) is introduced into the aerosampler with continuous wetting the walls of the microcentrifuges for another 5 min. The current drops to 7.5 nA, corresponding to a response of 1.8 nA. Then the supply of air is stopped, the biasing voltage is set to 100 mV and a BSL-solution (Phosphate Buffer Saline) with no viruses is injected from another container 3, whereby the viral particles are released from the sensors ("flush circle") until the current returns to 9.3 nA. At the time of 900 s the BSL-solution is stopped and air with a virus concentration of 400 nMol/l is introduced into the aerosampler. The current now drops to 5.4 nA, corresponding to a response of 3.9 nA. Then this detection and flushing cycle is repeated. The last detection cycle is run with air containing 800 nMol/l viruses. The current drops to 0.8 nA, corresponding to a response of 8.5 nA. Accordingly, the response is nearly linear to the virus concentration in the air.

If after a number of detection/flushing cycles the current does not return to the original value (in the example 9.3 nA) the aptamers are removed from the detection chamber by flowing concentrated H$_2$SO$_4$ through the detection chamber with subsequent removing the acid with deionized water and renewing the aptamer coverage of the working electrodes.

In this preferred embodiment there are at least four containers 3 containing deionized water, BSL-solution, concentrated H$_2$SO$_4$ and a refreshing solution providing aptamers.

R&D resulting in this patent application has been funded in part by National Research Council of Canada (NRCC) and supported by NIOSH, Cincinnati, Ohio, USA, by providing the detailed drawings of the tandem reverse flow cyclones.

The invention claimed is:

1. Device for real-time detection of aeropathogens comprising:
   an aerosampler comprising (i) an air inlet to intake a sample of air comprising a plurality of droplets, wherein the plurality of droplets comprises aeropathogens, and (ii) at least one collector tube to receive the sample of air and to collect the plurality of droplets, and capable of collecting simultaneously two size distributions of the aeropathogens,
   a microfluidic system comprising at least one container, piping and at least one micro pump for flowing a liquid, wherein the at least one container contains wetting liquid, wherein the at least one container is fluidly connected to the at least two collector tubes to supply the wetting liquid to wet inner walls of the at least two collector tubes,
   at least one viral detection chamber fluidly connected to the aerosampler to receive the plurality of droplets and to detect the aeropathogens in the plurality of droplets,
   wherein the at least one viral detection chamber comprises at least one working electrode and at least one counter electrode, wherein the at least one working electrode comprises one or more compounds that specifically bind to one or more portions of the aeropathogens,
   at least one electronic detection system electrically connected to the at least one viral detection chamber,
   wherein data receivable from the at least one electronic detection system is processed electronically,
   wherein the aerosampler further comprises:
   a dust collector for collecting dust present in the sample of air, and
   wherein the at least two collector tubes are two centrifugal collector tubes oriented in a direction of flow of the sample of air,
   wherein a first tube of the two centrifugal collector tubes is positioned closer to the flow of the sample of air than a second tube of the two centrifugal collector tubes, such that the sample of air enters the first tube and the second tube in sequence,
   wherein the plurality of droplets comprises a first set of droplets having a diameter of between two microns and 10 microns, and a second set of droplets having a diameter of up to five microns,
   wherein the first tube receives a first portion of the sample of air and the wetting liquid, thereby collecting the first set of droplets, and
   wherein the second tube receives a second portion of the sample of air and the wetting liquid, thereby collecting the second set of droplets.

2. The device according to claim 1, further comprising a plurality of containers containing the liquid, wherein the plurality of containers is fluidly connected to the viral detection chamber to supply the liquid directly to the viral detection chamber.

3. The device according to claim 1, wherein the at least one viral detection chamber comprises a straight upper inner wall and a straight lower inner wall parallel to each other, wherein the at least one working electrode is disposed on the lower inner wall, and wherein the at least one counter electrode is disposed on the upper inner wall opposite to the at least one working electrode, thereby forming at least one pair of electrodes that has an axis perpendicular to both the upper inner wall and the lower inner wall.

4. The device according to claim 3, wherein the at least one counter electrode is larger than the at least one working electrode, wherein the at least one pair of electrodes generates an electric field that is perpendicular to flow of the plurality of droplets through the at least one viral detection chamber, and wherein the at least one counter electrode and the at least one working electrode are biased with a voltage of between −300 millivolts and 50 millivolts.

5. The device according to claim 1, further comprising a plurality of pumps and a plurality of valves, and wherein operation of the pumps, the valves, and the electronic detection system are controlled electronically.

6. The device according to claim 1, wherein the at least one viral detection chamber comprises a plurality of viral detection chambers, wherein the at least one electronic detection system comprises a plurality of electronic detection systems, wherein each of the plurality of viral detection chambers is assigned an electronic detection system in the plurality of electronic detection systems, and wherein the electronic processing of the data from the plurality of electronic detection systems is performed in common.

7. The device according to claim 1, wherein the wetting liquid is conveyed from the aerosampler to the at least one viral detection chamber after catching the first set of droplets and the second set of droplets.

8. The device according to claim 1, wherein the at least one working electrode comprises a surface made of gold, wherein the one or more compounds are attached to the gold surface, and wherein the one or more compounds comprise one or more aptamers.

* * * * *